United States Patent
Yanagi et al.

[11] Patent Number: 5,873,834
[45] Date of Patent: Feb. 23, 1999

[54] BLOOD PRESSURE DETECTING DEVICE

[75] Inventors: Shinsaku Yanagi; Yoshinori Miyawaki; Yasuyuki Togoe, all of Kyoto, Japan

[73] Assignee: Omron Corporation, Kyoto, Japan

[21] Appl. No.: 812,746

[22] Filed: Mar. 6, 1997

[51] Int. Cl.$^6$ ............................................ A61B 5/00
[52] U.S. Cl. ............................ 600/485; 600/500
[58] Field of Search ........................... 600/485, 488, 600/490, 494–7, 500–503

[56] References Cited

U.S. PATENT DOCUMENTS

| | | | |
|---|---|---|---|
| 4,718,427 | 1/1988 | Russell | 600/494 |
| 4,907,596 | 3/1990 | Schmid et al. | 600/485 |
| 5,237,997 | 8/1993 | Gruebel et al. | 600/500 |
| 5,485,848 | 1/1996 | Jackson et al. | 600/500 |
| 5,533,511 | 7/1996 | Kaspari et al. | 600/494 |
| 5,564,427 | 10/1996 | Aso et al. | 600/494 |
| 5,590,649 | 1/1997 | Caro et al. | 600/500 |

FOREIGN PATENT DOCUMENTS 443267  8/1991  European Pat. Off. ............... 600/494

*Primary Examiner*—Robert L. Nasser
*Attorney, Agent, or Firm*—Morrison & Foerster LLP

[57] ABSTRACT

The blood pressure detecting device includes a blood pressure meter, a physiological detector, and a processing unit. The processing unit stores an equation to convert the value of the physiological data to the corresponding blood pressure value. To determine the equation during calibration, the patient's physiological data is measured several times in the course of normal activities in order to obtain an actual blood pressure value for each patient. To determine the equation during measurement mode, the patient measures the physiological data value as above, and then a customized equation stored in memory will convert the physiological value to the patient's blood pressure value. Therefore, the more calibration data are collected for an individual patient, the more accurate the equation will be made, and thus a more accurate measurement will be made.

13 Claims, 14 Drawing Sheets

FIG. 11

|  | SYS | DIA | PTT | b/a |
|---|---|---|---|---|
| CALIBRATION DATA SET A | 120 | 80 | 205 | 0.82 |
| CALIBRATION DATA SET B | 123 | 82 | 210 | 0.75 |
| CALIBRATION DATA SET C | 150 | 95 | 219 | 0.60 |
| ⋮ | ⋮ | ⋮ | ⋮ | ⋮ |
| ARBITRARY CALIBRATION DATA SET K | $SYS_0$ | $DIA_0$ | $PTT_0$ | $b_0/a_0$ |

FIG. 13

|  | SYS | DIA | PTT | b/a |  |
|---|---|---|---|---|---|
| CALIBRATION DATA SET A | 120 | 80 | 205 | 0.82 | NOT USED |
| CALIBRATION DATA SET B | 123 | 82 | 210 | 0.75 | USED |
| CALIBRATION DATA SET C | 150 | 95 | 219 | 0.60 | NOT USED |

BLOOD PRESSURE DETECTING DEVICE

BACKGROUND

The invention relates to a blood pressure detecting device that uses the relationship between blood pressure and other physiological data to estimate the blood pressure of a patient.

A conventional blood pressure detecting device may use physiological data such as the transit speed of a pulse to estimate a patient's blood pressure. In this indirect method, the blood pressure is estimated based on a known relationship between the blood pressure and the physiological data. The known relationship is based on blood pressure and physiological data for a large group of patients. This relationship may be calibrated to a patient by measuring the physiological data (e.g., the pulse transit speed) and the blood pressure of the patient while the patient is resting and while the patient is exercising actively.

SUMMARY

In one aspect, generally, the invention features a blood pressure detecting device having a physiological detector to detect physiological data that corresponds to a blood pressure value. A processor is configured to convert the physiological data to the blood pressure value by using a conversion equation and is configured to calibrate the conversion equation based on fluctuations of the relationship between the physiological data and the blood pressure.

Embodiments of the invention may include one or more of the following features. The physiological data may include a set of pulsewave transit time values, a set of cardiac pulse rate values, or a set of second-derivative pulsewave height values. The blood pressure value may include systolic pressure values or diastolic pressure values.

The blood pressure detecting device may include a blood pressure meter to measure the blood pressure value that corresponds to the physiological data. The processor may be configured to use the measured value and the corresponding physiological data to calibrate the conversion equation. The processor also may be configured to calibrate the conversion equation using a plurality of calibration data sets that each include physiological data and a corresponding blood pressure value. A memory, located in the processor, may store the plurality of calibration data sets.

The processor also may be configured to calculate an average value of a plurality of calibration data sets that exist within a predetermined range, to correct a slope of the conversion equation and calculate a regression line using the least square method. The processor may be configured to calibrate the conversion equation in different ways according to the number of calibration data sets and range of data.

Other features and advantages will become apparent from the following description, including the drawings, and from the claims.

BRIEF DESCRIPTION OF THE INVENTION

FIG. 11 is a chart of calibration data sets for the blood pressure detecting device of FIG. 10.

FIG. 13 is a chart of the calibration data sets of FIG. 11 indicating data sets that will be measured according to the graphs of FIGS. 12A and 12B.

DETAILED DESCRIPTION

Figure 1:
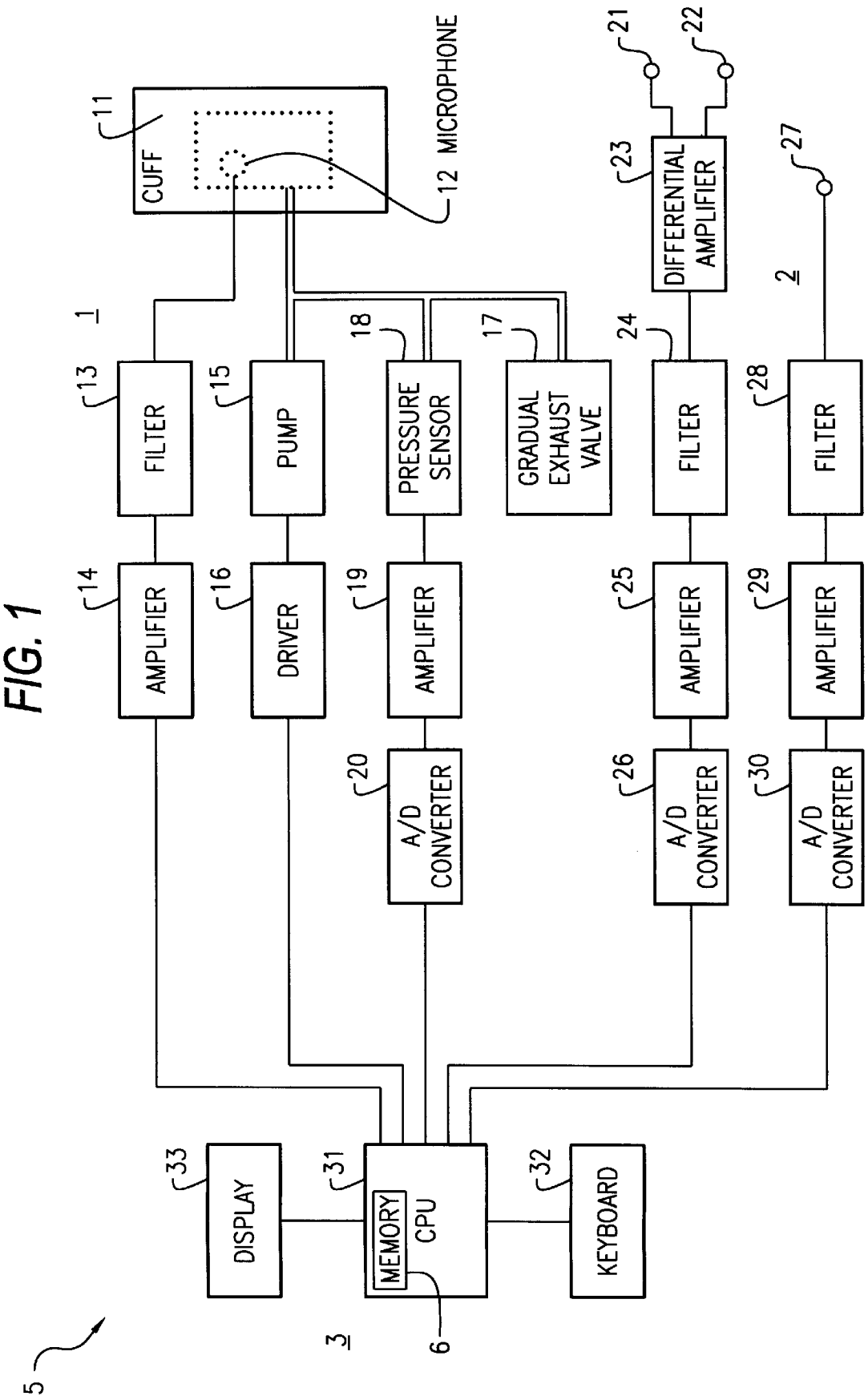
FIG. 1 is a block diagram of internal components of a blood pressure detecting device.

Referring to FIG. 1, a blood pressure detecting device 5 includes a blood pressure meter 1 for measuring blood pressure (BP) by pressurizing an artery, a physiological detector 2 for detecting an electrocardiogram waveform and a photoelectric pulsewave related to a patient's cardiac pulse, and a processing unit 3 for controlling the device 5. The device 5 is controlled by a central processing unit (CPU) 31 located inside the processing unit 3. The CPU 31 includes a memory 6 that stores the blood pressure values, as measured by the blood pressure meter 1, along with physiological data. The processing unit 3 also includes a keyboard 32 for inputting data and a display 33 for viewing the data.

The blood pressure meter 1 includes a cuff 11 to pressurize a blood vessel. A microphone 12 is located inside the cuff 11 and a signal from the microphone 12 is filtered through a filter 13 connected to the microphone 12. An amplifier 14, connected to the filter 13, amplifies the filtered signal and supplies the signal to the CPU 31. A driver 16, connected to pump 15 and the CPU 31, drives the pump 15 to pressurize the cuff 11. A pressure sensor 18 detects a pressure signal from the cuff 11. The cuff 11 is depressurized by a gradual exhaust valve 17. The pressure signal from the cuff 11 is amplified by an amplifier 19. An A/D converter 20 digitizes the amplified pressure signal and transmits the pressure signal to the CPU 31.

The physiological detector 2 includes two electrocardiograph electrodes 21 and 22. A differential amplifier 23, connected to the electrodes 21 and 22, amplifies an electrocardiograph signal produced by the electrodes. A filter 24, connected to the differential amplifier 23, filters noise from the electrocardiograph signal. The filtered electrocardiograph signal is amplified through an amplifier 25 connected to the filter 24. An AID converter 26 digitizes the amplified signal and transmits it to the CPU 31. The physiological detector 2 also includes a photoelectric pulsewave sensor 27 which connects to a fingertip of the patient. A filter 28 removes noise from a signal produced by the sensor 27, and an amplifier 29 amplifies the filtered signal. An A/D converter 30 digitizes the amplified photoelectric pulsewave signal and transmits the signal to the CPU 31.

The blood pressure meter 1 measures the blood pressure several times during the day by pressurizing the artery. At the same time, the physiological data are measured by the physiological detector 2. A blood pressure value and the physiological data are stored in the memory 6 as sets of calibration data. The calibration data are used to generate an equation representing the relationship between the physiological data and the blood pressure. During the measurement mode, the blood pressure is determined by applying an actual measured physiological data to the equation.

By measuring the blood pressure and the physiological data several times, in the course of normal activities, the system can capture daily fluctuation of the patient's blood pressure and physiological data. This enables the system to generate an updated equation characterizing the relationship between the blood pressure and the physiological data without imposing a significant burden on the patient, and thereby permits a highly accurate measurement of the blood pressure in an actual measurement mode. In addition, as more calibration data are accumulated for the patient, the accuracy with which the patient's blood pressure is measured increases.

Figure 2:
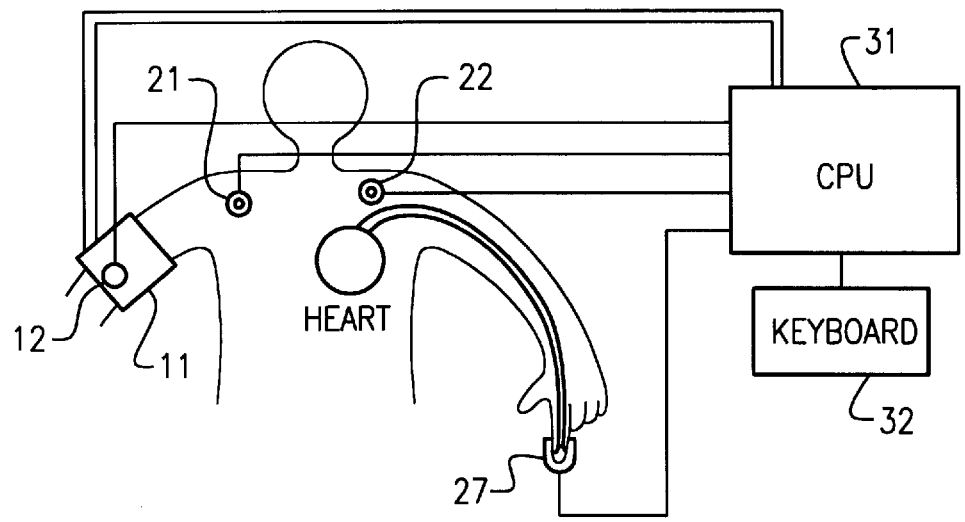
FIG. 2 is a schematic of positions of a cuff, electrocardiograph electrodes, and a pulsewave sensor of the blood pressure detecting device of FIG. 1 during calibration.

As shown in FIG. 2, during calibration, the device 5 is connected to the patient with the cuff 11 placed on the patient's upper arm and electrodes 21 and 22 placed on both sides of the patient's chest. The cuff 11, the microphone 12, and the electrodes 21 and 22 are each connected to the CPU 31. The photoelectric pulsewave sensor 27 is placed on the patient's finger. When calibration is performed, the blood pressure is measured by the blood pressure meter 1 and physiological data is measured by the physiological detector 2. Alternatively, the blood pressure can be measured separately by an external blood pressure meter. The blood pressure value, as measured by the external blood pressure meter, is input through the keyboard 32. The blood pressure value and the physiological data obtained during calibration are combined in a data set and stored as calibration data in the memory 6.

Figure 3:
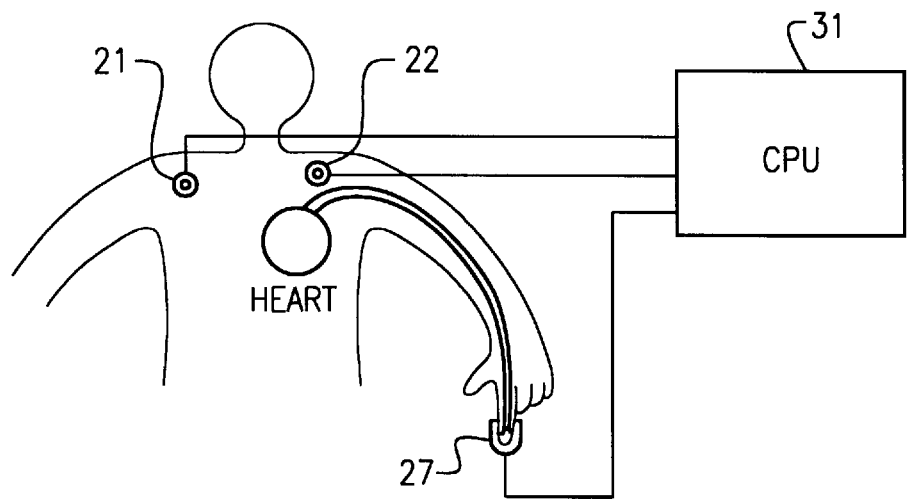
FIG. 3 is a schematic of positions of the cuff, the electrocardiograph electrodes and the pulsewave sensor of the blood pressure detecting device of FIG. 1. during measurement.

As shown in FIG. 3, during measurement, the device 5 is connected to the patient with the electrodes 21 and 22, and the photoelectric pulsewave sensor 27 connected to the CPU 31 in a manner similar to that shown in FIG. 2. When measurement is performed, the physiological data is measured by the physiological detector 2. The blood pressure value is obtained by inserting the physiological data into an equation relating the physiological data and the blood pressure value.

FIGS. 4–7 illustrate various methods of relating the blood pressure value to the physiological data according to the number and amplitude of fluctuations of the calibration data stored in the memory 6. In FIGS. 4–7, the pulsewave transit time (PTT) values are used as the physiological data. A cardiac pulserate (HR) or a second-derivative pulsewave height (Hv) also could be used. In addition, the blood pressure value (BP) that corresponds either to a systolic (SYS) or a diastolic (DIA) pressure is used.

Figure 4:
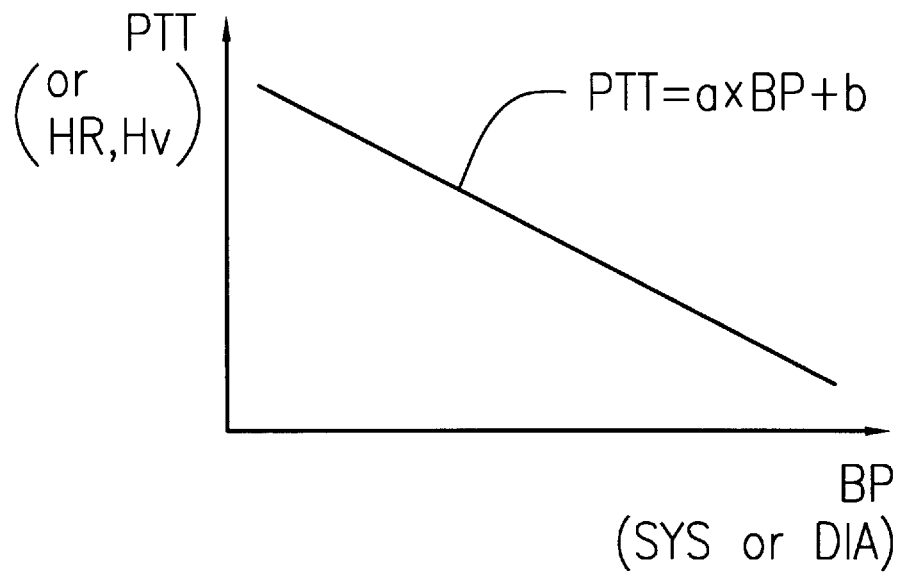
FIG. 4 is a graph of physiological data relative to blood pressure when no calibration data is available.

Referring to FIG. 4, when there is no calibration data, the blood pressure value and the pulsewave transit time value are related by a line having a slope a, and a y-intercept b. The values for the slope and the intercept are obtained from data collected from a plurality of patients using the following equation:

$$PTT = a*BP + b.$$

Once the equation relating the blood pressure value and the pulsewave transit time value is obtained, the actual blood pressure value can be determined from the physiological data.

Figure 5:
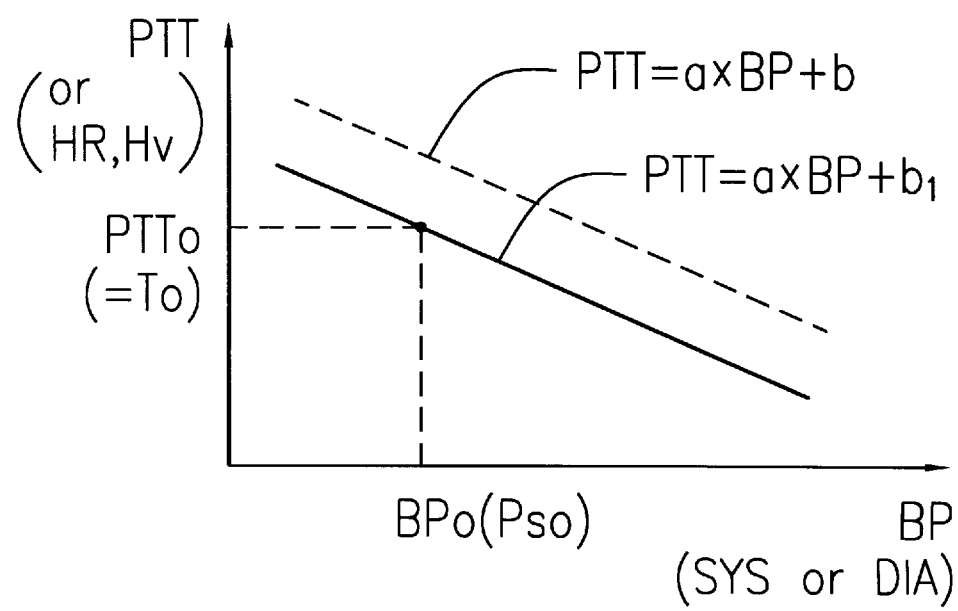
FIG. 5 is a graph of the physiological data relative to the blood pressure when one set of calibration data is available.

As shown in FIG. 5, when there is one set of calibration data $(Ps_0, T_0)$, the y-intercept of the time is adjusted to comply with the calibration data. The resulting relationship is expressed as:

$$PTT = a*BP + b_1,$$

where a is the slope based on standard data and $b_1 = T_0 - a*Ps_0$.

Figure 6:
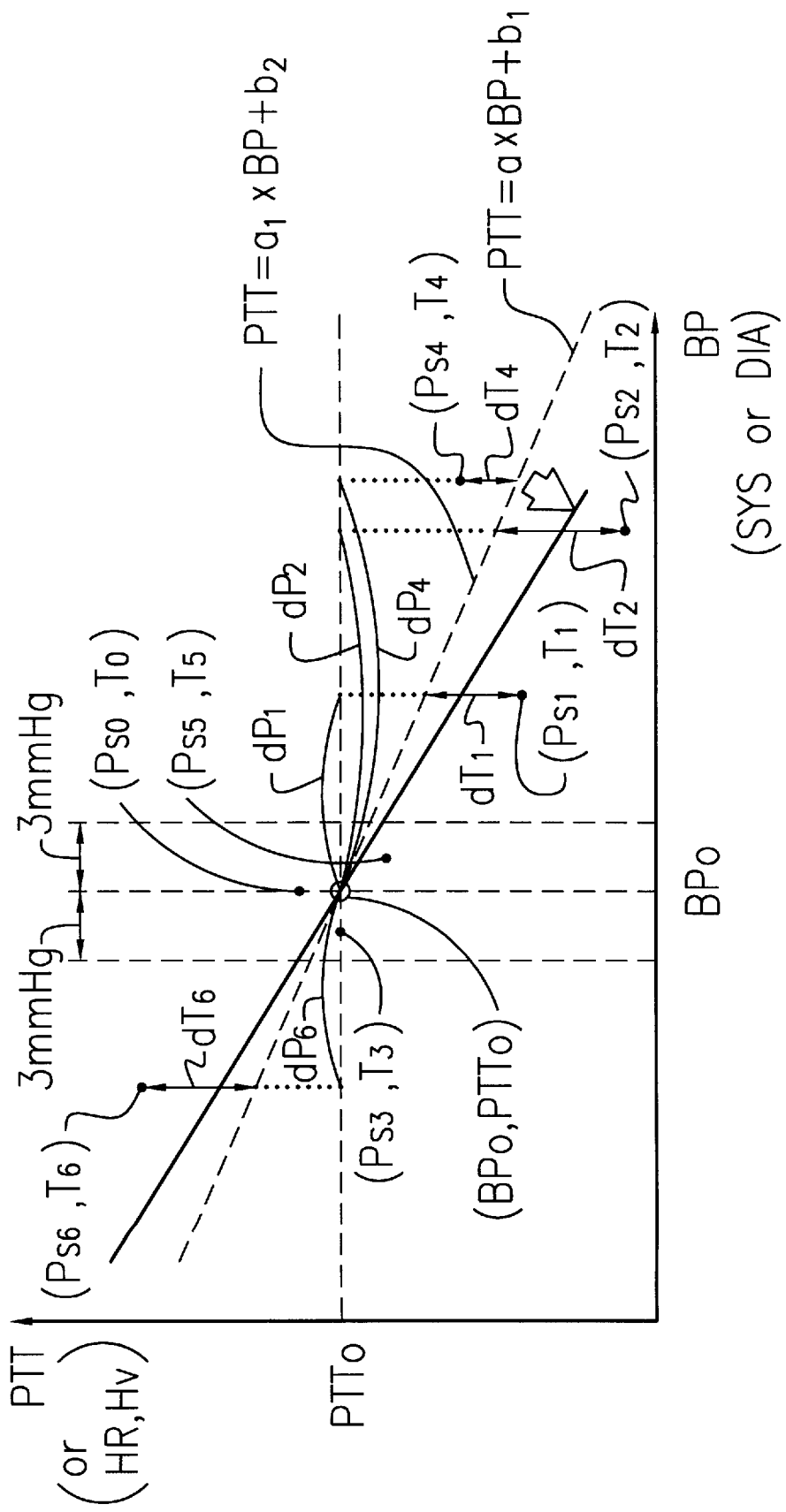
FIG. 6 is a graph of the physiological data relative to the blood pressure when two to ten sets of calibration data are available.

FIG. 6 illustrates a technique used when there are two or more sets of calibration data and a standard deviation of the blood pressure is less than or equal to 5 mm Hg. All calibration data with blood pressure values within a range of ±3 mm Hg from the oldest calibration data $(Ps_0)$ are detected. The detected calibration data are used to calculate an offset representative value. Average values of the blood pressure values and the pulsewave transit time values are used as offset representative values $(BP_0, PTT_0)$. An equation that passes through the offset representative values is obtained using the slope based on standard data:

$$PTT = a*BP + b_1,$$

where $b_1 = PTT_0 - a*BP_0$

Next, a new slope is determined using all calibration data that were not used to determine the offset $b_1$. The deviations of these data points from the line defined as $PTT = a*BP + b_1$ in the X and Y directions are determined and designated as $dT_n$ (where n is an integer corresponding to a pair of calibration data points) for the Y axis and $dP_n$ for the X axis. The average of $dT_n/dP_n$ is obtained and designated as $d_{ERR}$. The slope then is calibrated using $d_{ERR}$ to produce:

$$PTT = a_1*BP + b_2,$$

where $$a_1 = (1-\alpha)a + \alpha\, d_{ERR},$$

$$b_2 = PTT_0 - a_1*BP_0, \text{ and}$$

$\alpha$ is a proportional constant used to weigh the relative impact of a and $d_{ERR}$.

Figure 7:
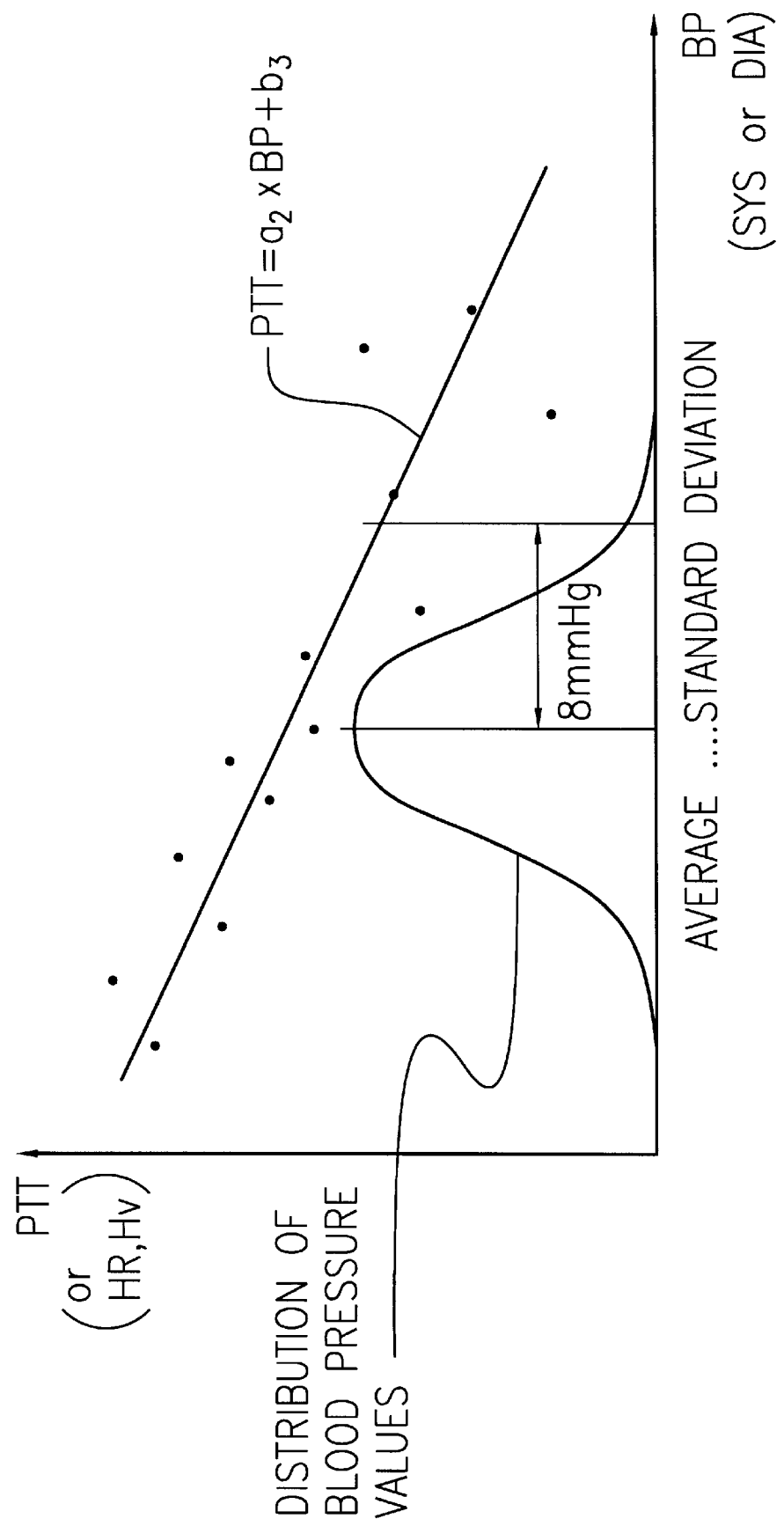
FIG. 7 is a graph of the physiological data relative to the blood pressure when more than ten sets of calibration data are available.

FIG. 7 illustrates a technique used when there are more than ten sets of calibration data and the standard deviation of the blood pressure is greater than 5 mm Hg. Using all the calibration data, a regression line is obtained using the least squares method. The relationship of the physiological data and the blood pressure is expressed as follows:

$$PTT = a_2*BP + b_3,$$

where $a_2$ and $b_3$ are constants derived from the regression line.

Figure 8:
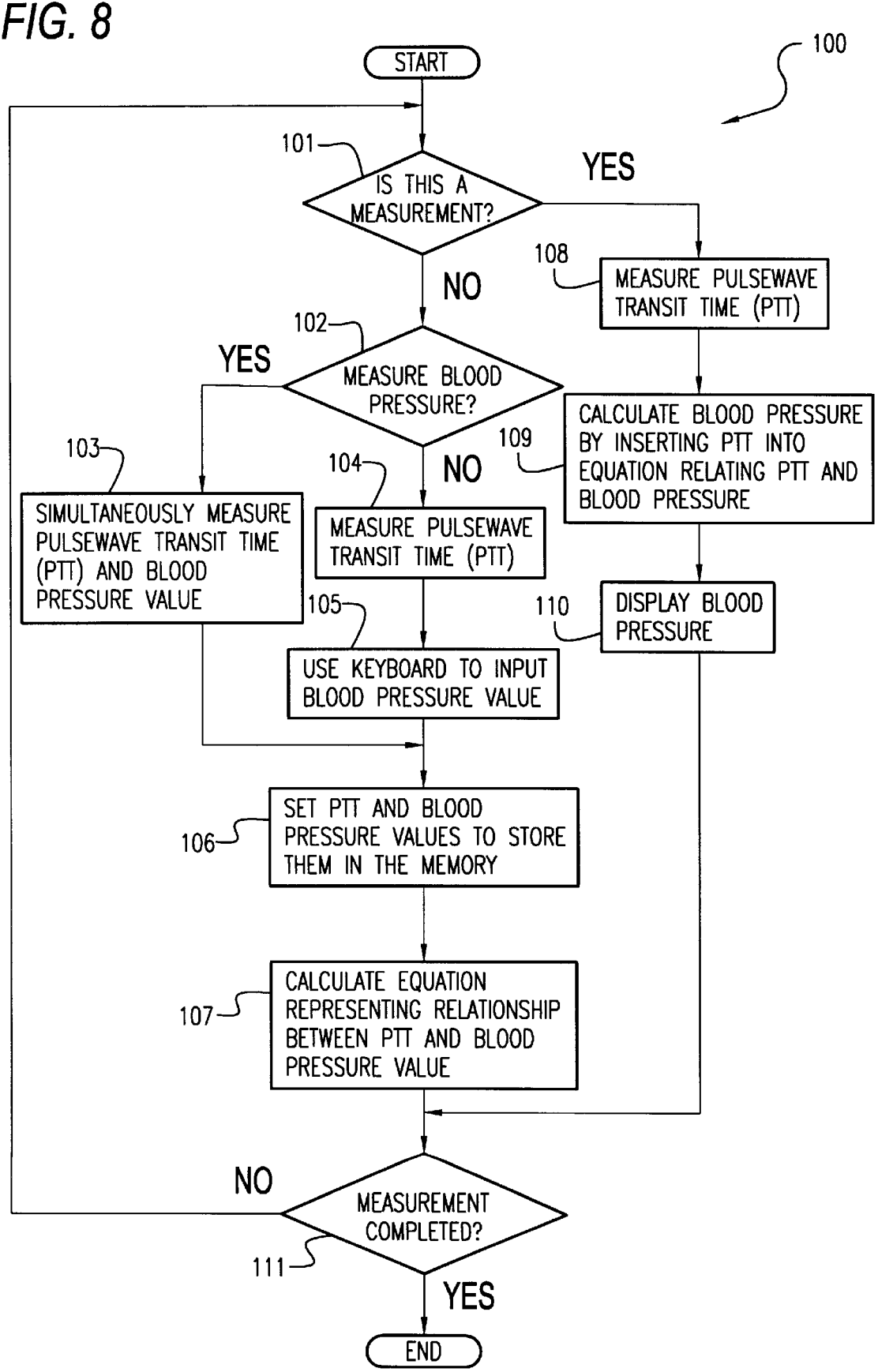
FIG. 8 is a flowchart of a procedure implemented by the blood pressure detecting device of FIG. 1.

Referring to FIG. 8, the processor 31 of the blood pressure detecting device 5 implements a procedure 100. Initially, the processor determines whether to operate the device 5 in a measurement mode (step 101). If not, the device 5 will operate in a calibration mode. If the device 5 is operating in the calibration mode, the processor 31 determines whether the blood pressure meter 1 should measure the blood pressure (step 102). If so, the blood pressure is measured simultaneously with the pulsewave transit time ("PTT") (step 103), where PTT is measured by the physiological detector 2. The blood pressure and the physiological data are measured at discretionary times during the patient's normal activities (e.g., once a day, every three days, once a week, after bathing, etc.)

If the blood pressure is not measured (step 102), only the pulsewave transit time is measured by the physiological detector 2 (step 104), and a blood pressure value obtained from an external meter is input to the device 5 through the keyboard 32 (step 105).

In either case, once the blood pressure value and the physiological data are obtained, they are stored as calibration data in the memory 6 of the CPU 31 (step 106). If the memory 6 is full, the oldest calibration data is erased. Next, an equation relating the blood pressure value and the physiological data is calculated according to the number of calibration data sets available and the range of data (step 107).

Returning to step 101, if the device 5 is operating in the measurement mode, the device 5 measures only the pulsewave transit time (step 108). Next, the pulsewave transit time value is input into an equation relating the physiological data and the blood pressure value to obtain a blood pressure value for the patient (step 109). The blood pressure value then is displayed on the display 33 (step 110).

After calculating the equation (step 106) or displaying the blood pressure (step 110), the processor 31 determnines if measurements are completed (step 11 1). If measurements are not completed, the device returns to step 101. Otherwise, the procedure 100 ends.

Figure 9:
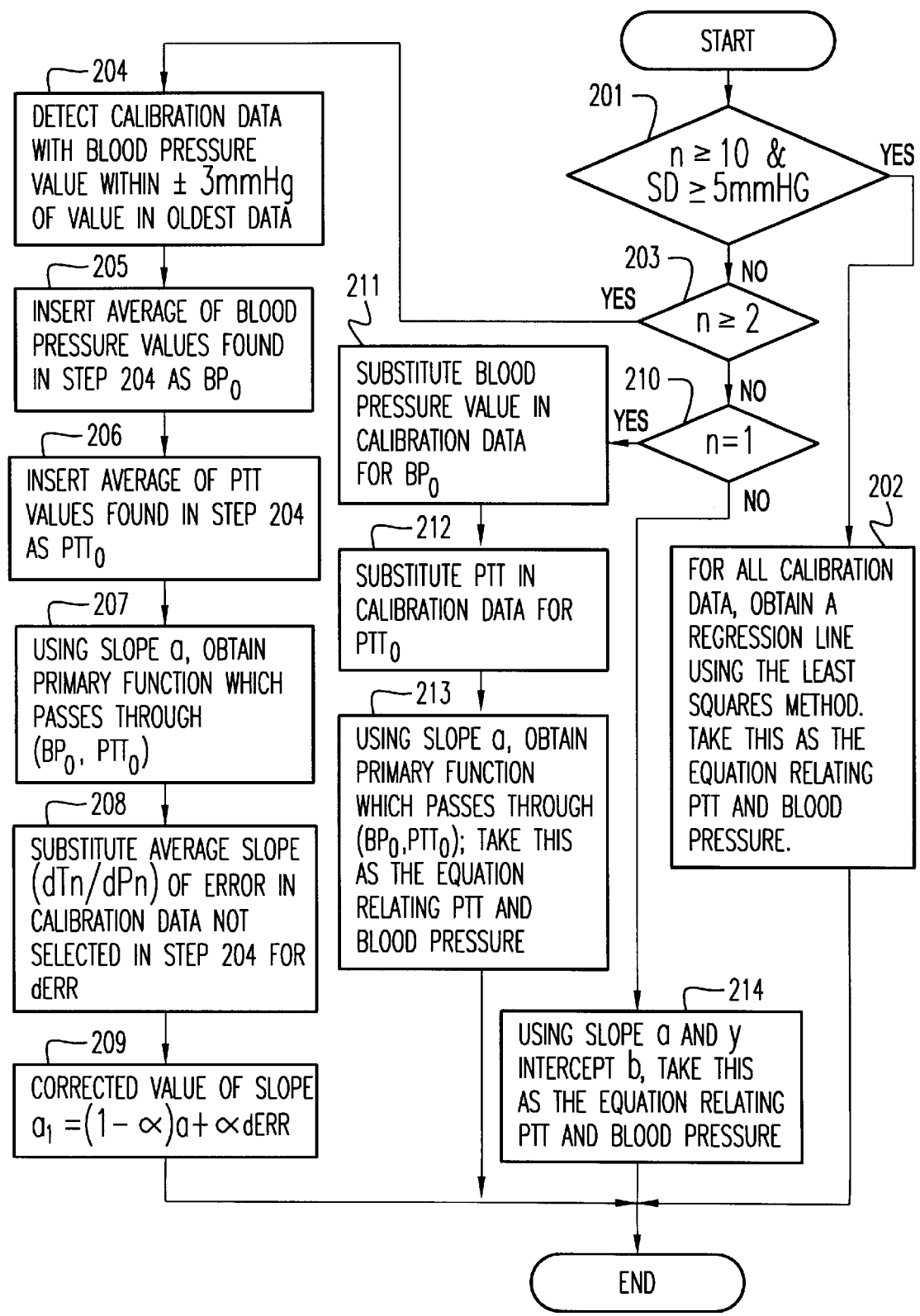
FIG. 9 is a flowchart of a procedure to calculate a relationship between the physiological data and blood pressure value.

Referring to FIG. 9, the processor 31 implements a procedure 200 to calculate the relationship between the physiological data and the blood pressure value. Initially, the processor determines whether there are ten or more sets of calibration data and whether a standard deviation (SD) of the blood pressure is at least 5 mm Hg (step 201). If so, the processor obtains a regression line for all of the calibration data using the least squares method and selects the regression line as the equation characterizing the relationship between the physiological data and the blood pressure value for the patient (step 202).

If there are less than ten sets of calibration data or if the standard deviation is less than 5 mm Hg, then the processor 31 determines if there are two or more sets of calibration data (step 203). If so, then all calibration data having blood pressure values within ±3 mm Hg of the oldest calibration data are detected (step 204). Next, an average of the detected blood pressure values (step 205) and an average of the detected physiological data (step 206) are calculated, and designated, respectively, as $BP_0$ and $PTT_0$. Using a statistically obtained slope, a primary function which passes through $(B_0, PTT_0)$ is obtained (step 207). Next, average differences $(dT_n/dP_n)$ from the obtained primary function for calibration data that were not detected at step 204 are determined, and a ratio of these differences $(dT_n/dP_n)$ is designated as $d_{ERR}$ (step 208). A corrected slope is then determined as $a_1=(1-\alpha)a+\alpha d_{ERR}$ (step 209). This equation expresses the relationship between the physiological data and the blood pressure.

If there are less than two sets of calibration data (step 203), the processor determines if there is at least one set of calibration data (step 210). If so, the blood pressure value in the set of calibration data is used as $BP_0$ (step 211), the physiological data value in the set of calibration data is used as $PTT_0$ (step 212), and a primary function which passes through $(BP_0, PTT_0)$ is obtained using a statistically determined slope a (step 213).

If there is no calibration data (step 210), a primary function is generated using a statistically obtained slope a and y-intercept b (step 214).

Figure 10:
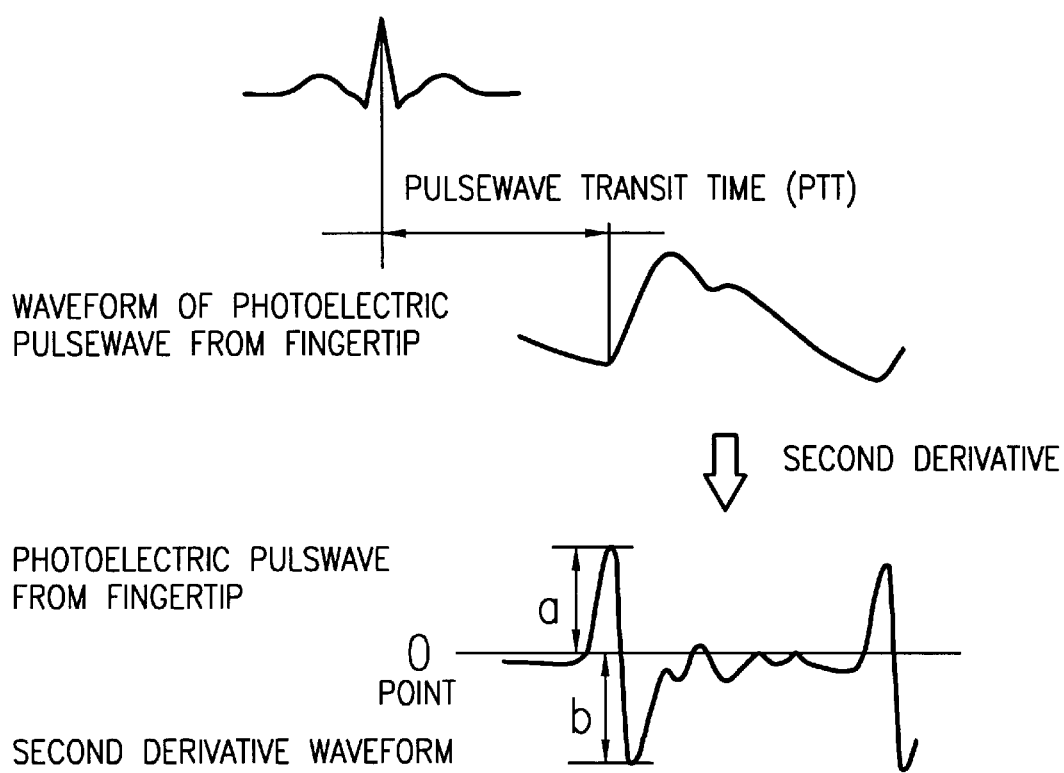
FIG. 10 is a graph of physiological data used by another blood pressure detecting device.

Other embodiments are within the scope of the following claims. For example, as an alternative to calculating the physiological data and the blood pressure value using a first derivative, the device 5 can calculate the data and the value using a second derivative. The configuration of the hardware and the arrangement of the components during calibration and measurement are the same as was previously discussed with respect to FIGS. 1–3. Referring to FIG. 10, a graph illustrates the physiological data and a height of a second derivative waveform (b/a). In addition to the previous types of physiological data, many other types of data could also be used as the physiological data, such as heart rate, baseline oscillation period, rise time of pulsewave, or primary derivative pulsewave of the photoelectric waveform.

FIGS. 11–14 illustrate a procedure by which unsuitable data are removed from the calibration data and a new equation expressing the relationship between the physiological data and the blood pressure value is calculated for an individual patient. According to this procedure, the blood pressure value obtained by the device 5 or one that is input manually and the physiological data corresponding to the pressure are combined in a data set and stored in memory 6 as calibration data for the individual patient.

In particular, FIG. 11 shows a chart of calibration data sets A, B, C, . . . , K. The values in calibration data set K are the average values of all the data at the centers of their distribution. Therefore calibration data set K is used as a reference by device 5.

Figure 12A:
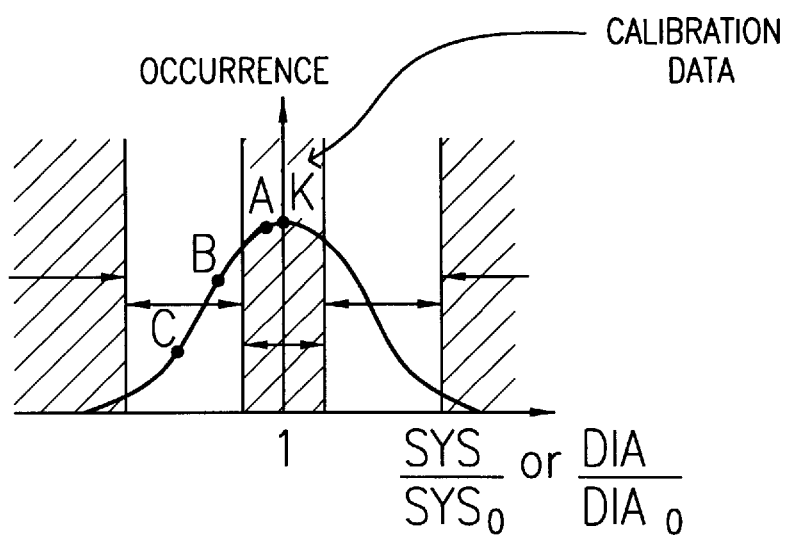
FIGS. 12A and 12B illustrate a set of graphs of the calibration data sets of FIG. 11 illustrating ratios of the calibration data (FIG. 12A) and difference in the calibration data (FIG. 12B).
Figure 12A:
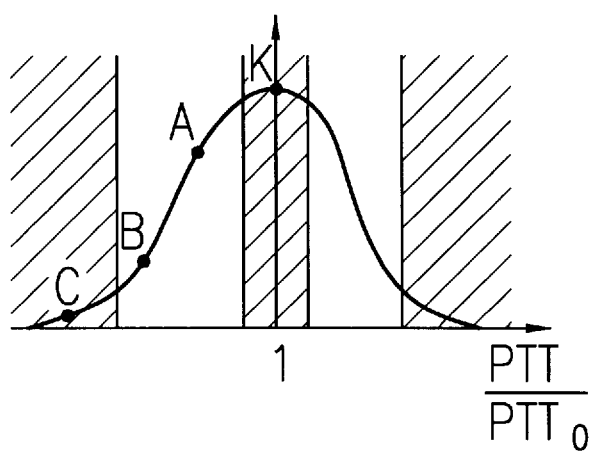
Figure 12A:
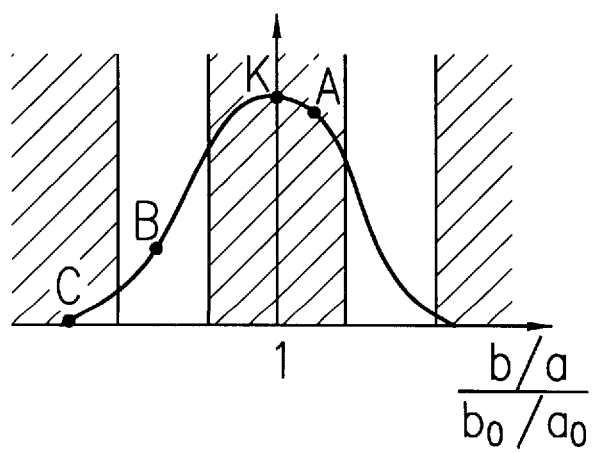
Figure 12B:
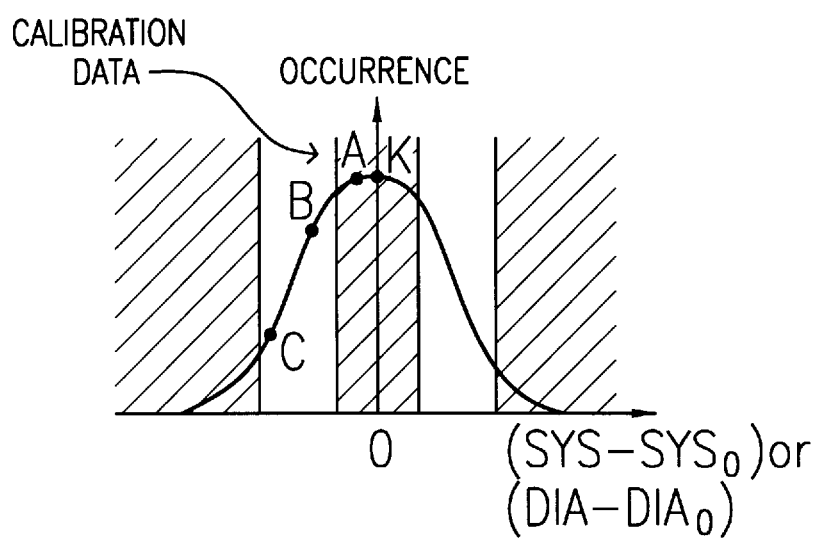
Figure 12B:
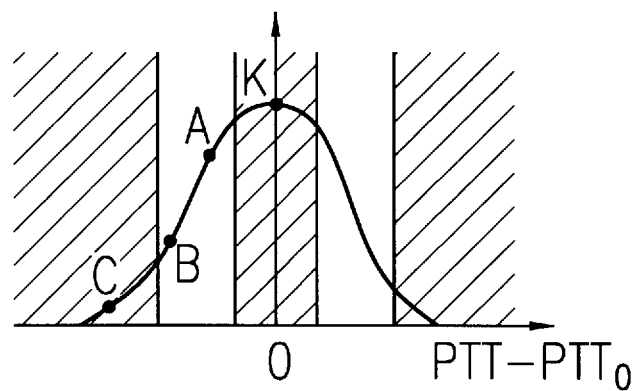
Figure 12B:
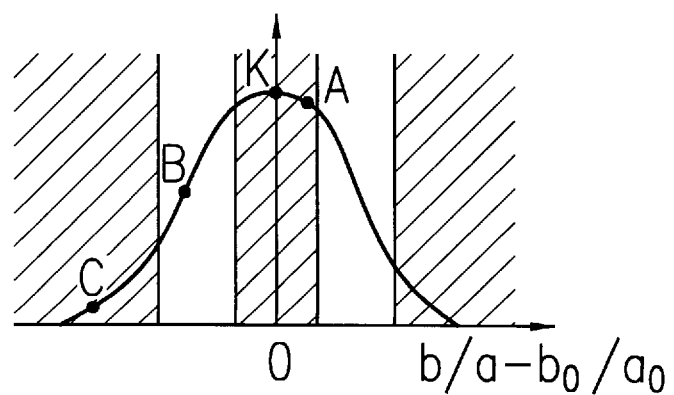

The graphs of FIGS. 12A and 12B illustrate for each element of the calibration data sets (SYS, DIA, PUT, and b/a), the ratio of the value in each data set to the corresponding value in the K data set (FIG. 12A) and the difference between the value in each data set to the corresponding value in the K data set (FIG. 12B). If the difference or ratio of the calibration data set is less than a given range of the average value, then the variation is considered to be deficient, and the data set containing such elements is considered defective. If the difference or ratio of the calibration data is greater than the given range of the average value, the variation is considered to be abnormally large, and the data set containing such elements is considered defective. For example, the calibration data of set A for elements SYS, DIA and b/a are considered to be less than the given range of the average value and is therefore not used for measurement. Similarly, the calibration data of set C for elements PTT and b/a are considered to be greater than the given range of the average value and are not used for measurement. Only the calibration data of set B are within the given range of the average value for all of the elements and will be used for measurement. FIG. 13 shows which calibration data sets are to be used for measurement and which will not be used. The defective data sets (A and C) are stored in the memory 6 and the remaining data set (B) are used for measurement.

Figure 14:
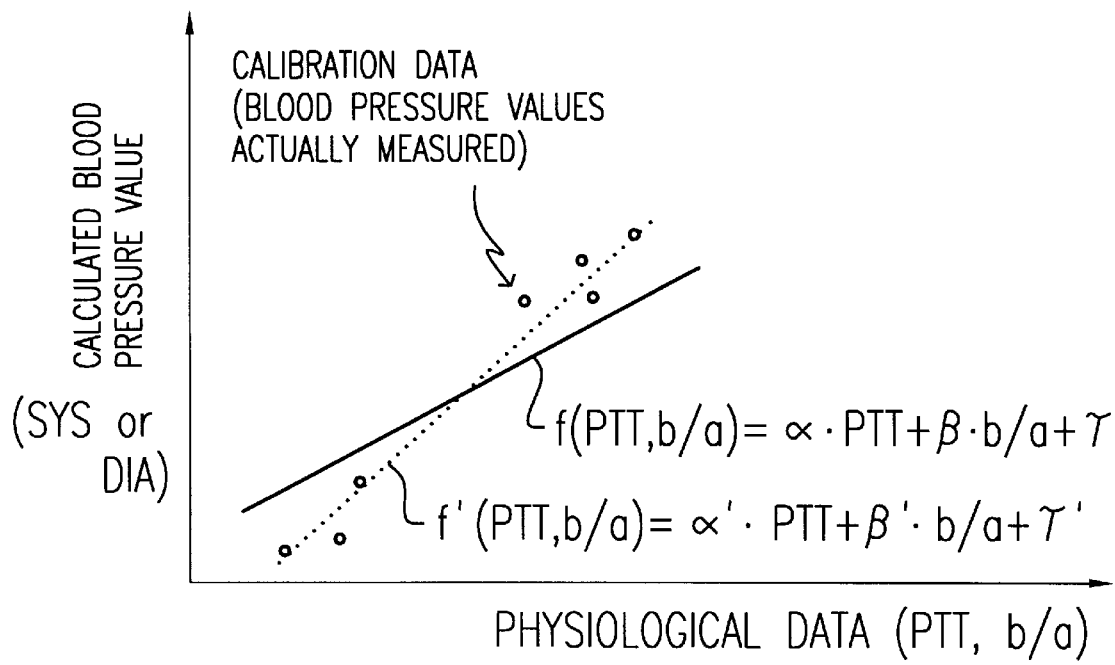
FIGS. 14 and 15 are graphs of physiological data relative to blood pressure value for the blood pressure detecting device of FIG. 10.

FIG. 14 shows the relationship between the physiological data and the blood pressure value. If no calibration data coefficients $\alpha$, $\beta$ and $\gamma$ are obtained from the data of the patients, a standard equation based on unspecified patients is determined as follows:

$$BP\ (SYS\ or\ DIA) = \alpha * PTT + \beta * (b/a) + \gamma,$$

where the coefficients $\alpha$, $\beta$ and $\gamma$ are standard values and the blood pressure (BP) corresponds either to the systolic (SYS) or diastolic (DIA) pressure.

In an actual measurement, an arbitrary set of calibration data is chosen as a reference. The arbitrary point can be substituted in the equation to derive the blood pressure value. If there are at least two good data sets remaining, regardless of whether any defective data sets have been removed, new coefficients $\alpha'$, $\beta'$ and $\gamma'$ are derived in order to minimize the square error between the actually measured blood pressure value and the calculated blood pressure value. A new equation is therefore calculated that is customized for the particular patient.

Figure 15:
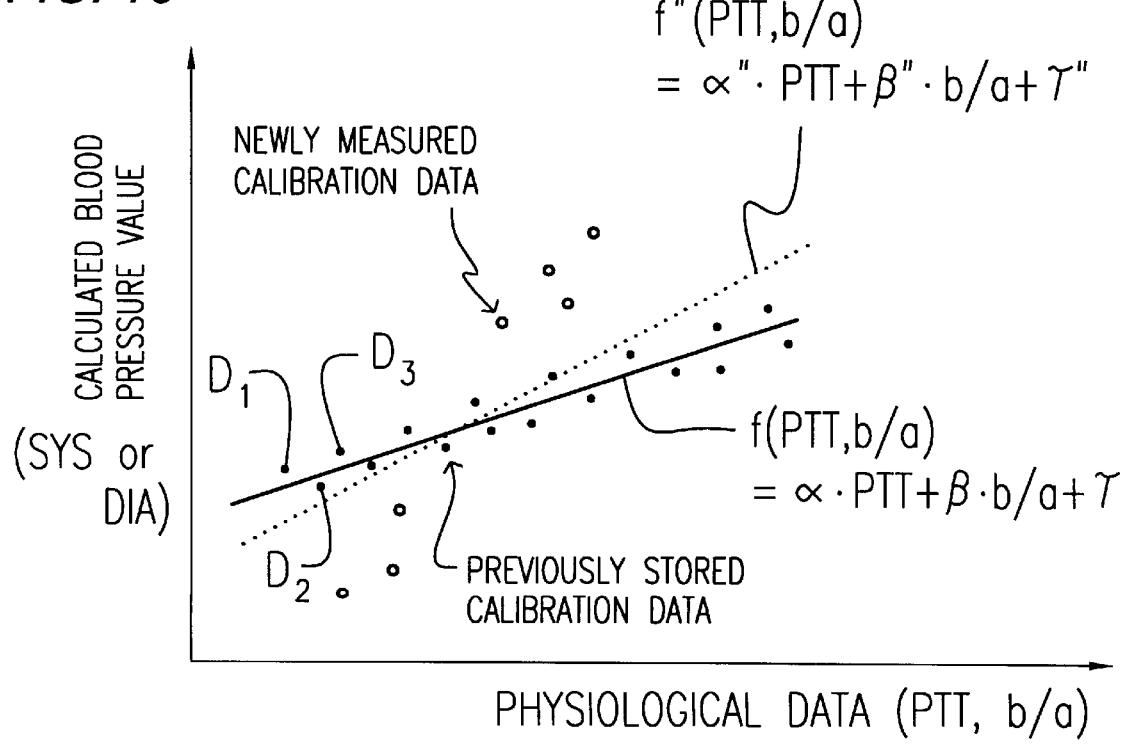

Alternatively, as shown in FIG. 15, calibration data $D_1$, $D_2$, $D_3$, etc., which are used to calculate the equation for the unspecified patient, can be stored in the memory 6. The good calibration data for each individual can be added to the stored data in order to construct a new set of calibration data. Each time the new set of calibration data is updated, new coefficients $\alpha''$, $\beta''$ and $\gamma''$ are derived in order to minimize the square error between the actually measured blood pressure value and the calculated blood pressure value. Therefore, the equation for the unspecified patient, can be customized successively for each individual equation for each patient.

Figure 16:
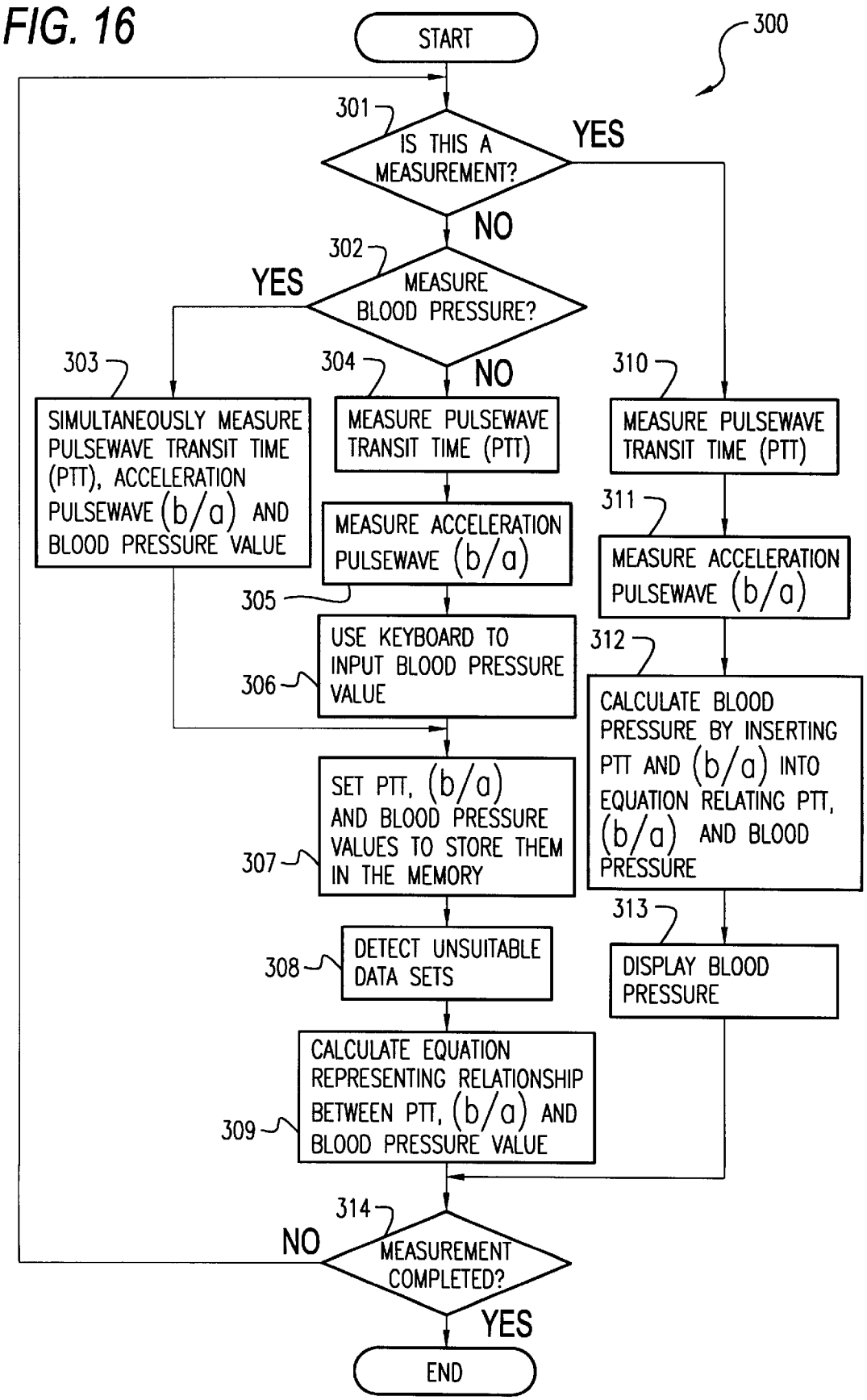
FIG. 16 is a flowchart of a procedure implemented by the blood pressure detecting device of FIG. 10.

Referring to FIG. 16, the processor 31 implements a procedure 300. Initially, the processor determines whether to operate in a measurement mode (step 301). If not, the device operates in a calibration mode. In the calibration mode, the processor determines whether the blood pressure meter 1 should measure the blood pressure (step 302). If so, the blood pressure is measured simultaneously with the pulse-wave transit time and the second derivative waveform of the photoelectric pulsewave (b/a), where the PTT and b/a are measured by the physiological detector 2 (step 303).

If the blood pressure is not measured (step 302), only the pulsewave transit time (step 304) and an acceleration pulsewave b/a (step 305) are measured by the physiological detector 2. A blood pressure value then is obtained by measuring the blood pressure with an external meter and supplying the value manually through the keyboard 32 (step 306).

After the values are obtained (step 303 or step 306), the blood pressure value, the pulsewave transit time, and the acceleration pulsewave are stored as calibration data in the memory 6 of the CPU 31 (step 307). The device then detects defective calibration data as discussed previously with respect to FIGS. 12A and 12B (step 308). Next, a new equation expressing the relationship of the blood pressure and the physiological data is calculated using the calibration data (step 309).

When operating in the measurement mode, the device 5 measures the pulsewave transit time (step 310) and the acceleration pulsewave (step 311). The values for the PTT and b/a then are placed into the equation expressing the relationship between the physiological data and the blood pressure value to obtain a blood pressure value (step 312). The blood pressure value is shown on the display 33 (step 313).

After calculating the equation (step 309) or displaying the blood pressure (step 313), the device 5 determines whether the measurement has been completed. If not, the device 5 returns to step 301. If so, the procedure 300 ends.

What is claimed is:

1. A blood pressure detecting device, comprising:
   a physiological detector for detecting physiological data corresponding to a blood pressure value; and
   a processor configured to convert the physiological data to the blood pressure value using a conversion equation, wherein the processor is further configured to calibrate the conversion equation according to a number of calibration data sets, wherein said calibration data sets include the physiological data and a corresponding blood pressure value.

2. The blood pressure detecting device of claim 1, further comprising an blood pressure meter for measuring a blood pressure value corresponding to physiological data, wherein the processor is configured to use the measured value and the corresponding data to calibrate the conversion equation.

3. The blood pressure detecting device of claim 1, wherein the processor is configured to calibrate the conversion equation using a plurality of calibration data sets that each include physiological data and a corresponding blood pressure value.

4. The blood pressure detecting device of claim 3, wherein the processor comprises a memory that stores the plurality of calibration data sets.

5. The blood pressure detecting device of claim 3, wherein the processor is configured to calibrate the conversion equation according to the number of calibration data sets and range of the data.

6. The blood pressure detecting device of claim 1, wherein the processor is configured to:
   calculating an average value of a plurality of calibration data sets that exist within a predetermined range;
   correct a slope of the conversion equation; and
   calculate a regression line using least squares method.

7. The blood pressure detecting device of claim 1, wherein the physiological data includes a set of pulsewave transit time values.

8. The blood pressure detecting device of claim 1, wherein the physiological data includes a set of cardiac pulse rate values.

9. The blood pressure detecting device of claim 1, wherein the physiological data includes a set of second-derivative pulsewave height values with respect to time.

10. The blood pressure detecting device of claim 1, wherein the blood pressure value includes a systolic pressure value.

11. The blood pressure detecting device of claim 1, wherein the blood pressure value includes a diastolic pressure value.

12. The blood pressure detecting device of claim 1, wherein the physiological detector comprises a photoelectric pulsewave sensor that connects to a fingertip of a patient.

13. The blood pressure detecting device of claim 1, further comprising an external blood pressure meter for measuring the blood pressure value.

* * * * *